United States Patent

Ishida et al.

(10) Patent No.: US 10,238,585 B2
(45) Date of Patent: Mar. 26, 2019

(54) OIL-IN-WATER EMULSION SUNSCREEN COSMETIC

(71) Applicants: Kahori Ishida, Yokohama (JP); Taichi Harada, Yokohama (JP); Yosuke Ikebe, Yokohama (JP)

(72) Inventors: Kahori Ishida, Yokohama (JP); Taichi Harada, Yokohama (JP); Yosuke Ikebe, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/353,497

(22) PCT Filed: Oct. 10, 2012

(86) PCT No.: PCT/JP2012/076185
§ 371 (c)(1),
(2) Date: Apr. 23, 2014

(87) PCT Pub. No.: WO2013/061776
PCT Pub. Date: May 2, 2013

(65) Prior Publication Data
US 2014/0255323 A1 Sep. 11, 2014

(30) Foreign Application Priority Data

Oct. 27, 2011 (JP) ................................ 2011-235612

(51) Int. Cl.
| | | |
|---|---|---|
| *A61K 8/60* | (2006.01) | |
| *A61K 8/06* | (2006.01) | |
| *A61K 8/27* | (2006.01) | |
| *A61K 8/29* | (2006.01) | |
| *A61Q 17/04* | (2006.01) | |
| *A61K 8/36* | (2006.01) | |
| *A61K 8/58* | (2006.01) | |
| *A61K 8/73* | (2006.01) | |
| *A61K 8/891* | (2006.01) | |

(52) U.S. Cl.
CPC ............. *A61K 8/062* (2013.01); *A61K 8/27* (2013.01); *A61K 8/29* (2013.01); *A61K 8/361* (2013.01); *A61K 8/585* (2013.01); *A61K 8/60* (2013.01); *A61K 8/731* (2013.01); *A61K 8/891* (2013.01); *A61Q 17/04* (2013.01); *A61K 2800/30* (2013.01); *A61K 2800/623* (2013.01)

(58) Field of Classification Search
CPC ................................ A61K 8/062; A61K 8/585
See application file for complete search history.

(56) References Cited

U.S. PATENT DOCUMENTS

| | | | | |
|---|---|---|---|---|
| 5,188,831 A | * | 2/1993 | Nicoll et al. | 424/401 |
| 6,264,963 B1 | * | 7/2001 | Leifheit | A61K 8/31 |
| | | | | 424/401 |
| 2005/0207999 A1 | | 9/2005 | Vernaire | |
| 2007/0253989 A1 | * | 11/2007 | Abe et al. | 424/401 |
| 2011/0129509 A1 | | 6/2011 | Yoshida | |

FOREIGN PATENT DOCUMENTS

| | | |
|---|---|---|
| JP | H09-255543 A | 9/1997 |
| JP | 2005-145972 A | 6/2005 |
| JP | 2005-247722 A | 9/2005 |
| JP | 2007-277191 A | 10/2007 |
| JP | 2010-222349 A | 10/2010 |
| JP | 2011-136965 A | 7/2011 |
| WO | 2010-070867 A1 | 6/2010 |
| WO | WO-2010/149798 | * 12/2010 ............... A61K 8/02 |

OTHER PUBLICATIONS

The International Bureau of WIPO, "Notification of Transmittal of Translation of the International Preliminary Report on Patentability," issued in International Application No. PCT/JP2012/076185, of which U.S. Appl. No. 14/353,497 is a U.S. national phase entry, dated May 8, 2014.

* cited by examiner

*Primary Examiner* — Sreenivasan Padmanabhan
*Assistant Examiner* — Danielle Sullivan

(57) ABSTRACT

The present invention is intended to provide an organic UV absorber-free, non-chemical sunscreen cosmetic that contains hydrophobized zinc oxide and/or hydrophobized titanium dioxide as a UV scattering agent, specifically an oil-in-water emulsion sunscreen cosmetic that provides excellent emulsion stability and an excellent pleasant feel while maintaining high levels of UV protection.

5 Claims, 1 Drawing Sheet

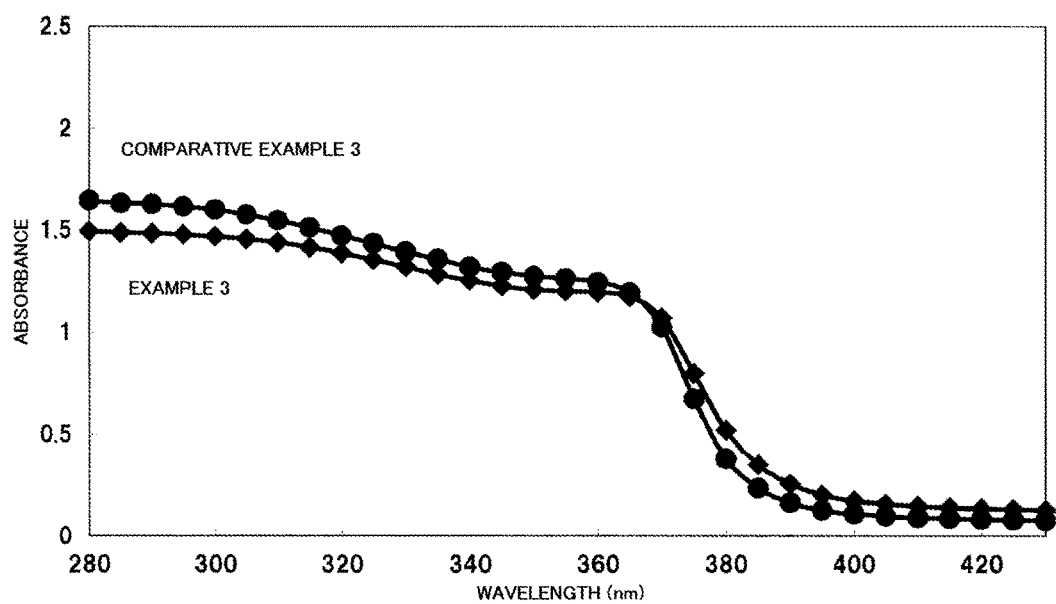

OIL-IN-WATER EMULSION SUNSCREEN COSMETIC

CROSS REFERENCE TO RELATED APPLICATIONS

This patent application is a U.S. national stage application under 35 U.S.C. § 371 of International Patent Application No. PCT/JP2012/076185 filed on Oct. 10, 2012, which claims the benefit of foreign priority to Japanese Patent Application No. JP 2011-235612 filed on Oct. 27, 2011, the disclosures of all of which are hereby incorporated by reference in their entireties. The International Application was published in Japanese on May 2, 2013, as International Publication No. WO 2013/061776 A1 under PCT Article 21(2).

TECHNICAL FIELD

The present invention relates to oil-in-water emulsion sunscreen cosmetics. Specifically, the invention relates to an organic UV absorber-free, non-chemical sunscreen cosmetic that contains hydrophobized zinc oxide and/or hydrophobized titanium dioxide as a UV scattering agent, and in which the hydrophobized zinc oxide and/or hydrophobized titanium dioxide are homogeneously and stably dispersed in the oil phase to provide excellent emulsion stability and an excellent pleasant feel.

BACKGROUND ART

Oil-in-water emulsion sunscreen cosmetics containing a hydrophobized UV scattering agent dispersed in an internal phase are useful as a formulation that can satisfy both a pleasant moisturizing feel and a high SPF.

Zinc oxide and titanium dioxide are commonly used as UV scattering agents (for example, Patent Citation 1). However, a technique that homogeneously and stably disperses zinc oxide and titanium dioxide in the oil component becomes very important in stably containing these zinc oxide and titanium dioxide components in the internal oil phase of an oil-in-water emulsion cosmetic.

On the other hand, sunscreen cosmetics (non-chemical sunscreens) that contain no organic UV absorber generally have drawbacks in terms of feeling. Specifically the products give a powdery or dry feel because of the UV scattering agent dispersed in the external oil phase of the water-in-oil emulsion composition. Patent Citation 2 discloses an organic UV absorber-free, non-chemical water-in-oil sunscreen cosmetic that contains a volatile component, an organic modified clay mineral, a spherical resin powder, a coating agent, and a UV scattering agent (zinc oxide and/or titanium dioxide). However, because the UV scattering agent is dispersed in the external oil phase of the water-in-oil composition, this cosmetic also has a very uncomfortable powdery or dry feel.

CITATION LIST

Patent Literature

Patent Citation 1: JP 2010-222349 A
Patent Citation 2: JP H9-255543 A

SUMMARY OF INVENTION

Technical Problem

Under these circumstances, the present inventors conducted intensive studies to provide an organic UV absorber-free, non-chemical sunscreen cosmetic that contains hydrophobized zinc oxide and/or hydrophobized titanium dioxide as a UV scattering agent, and in which excellent emulsion stability and an excellent pleasant feel can be realized by the high dispersibility of the hydrophobized zinc oxide and/or hydrophobized titanium dioxide. It was found after these studies that a sunscreen cosmetic with an oil-in-water emulsion composition containing a combination of specific components can provide an organic UV absorber-free, non-chemical oil-in-water emulsion sunscreen cosmetic in which large amounts of hydrophobized zinc oxide and/or hydrophobized titanium dioxide can be stably dispersed in the internal oil phase, and which has excellent emulsion stability (UV scattering agent dispersion stability) and an excellent pleasant feel while maintaining high levels of UV protection. The present invention was completed on the basis of this finding.

It is an object of the present invention to provide an organic UV absorber-free, non-chemical sunscreen cosmetic that contains hydrophobized zinc oxide and/or hydrophobized titanium dioxide as a UV scattering agent, specifically an oil-in-water emulsion sunscreen cosmetic that provides excellent emulsion stability and an excellent pleasant feel while maintaining high levels of UV protection.

Solution to Problem

Specifically, the present invention provides an organic UV absorber-free, oil-in-water emulsion sunscreen cosmetic that includes:

(A) zinc oxide and/or titanium dioxide hydrophobized with octyltriethoxysilane and/or dimethylpolysiloxane;
(B) a liquid higher fatty acid;
(C) a silicone of a structure containing a carboxyl group, or a sugar ester;
(D) a non-ionic surfactant;
(E) sodium carboxymethyl cellulose; and
(F) water.

In the oil-in-water emulsion sunscreen cosmetic provided by the present invention, the contents of the components (A) to (E) with respect to the total amount of the oil-in-water emulsion sunscreen cosmetic are:

3 to 35 mass % for (A) the zinc oxide and/or the titanium dioxide hydrophobized with octyltriethoxysilane and/or dimethylpolysiloxane;
0.1 to 2 mass % for (B) the liquid higher fatty acid;
0.1 to 1.5 mass % for (C) the silicone of a structure containing a carboxyl group, or the sugar ester;
0.5 to 4.5 mass % for (D) the non-ionic surfactant; and
0.1 to 1 mass % for (E) the sodium carboxymethyl cellulose.

Advantageous Effects of Invention

The present invention can provide an organic UV absorber-free, non-chemical sunscreen cosmetic that contains hydrophobized zinc oxide and/or hydrophobized titanium dioxide as a UV scattering agent, specifically an oil-in-water emulsion sunscreen cosmetic that provides excellent emulsion stability and an excellent pleasant feel while maintaining high levels of UV protection.

BRIEF DESCRIPTION OF DRAWINGS

FIG. 1 represents UV spectra of Example 3 and Comparative Example 3.

DESCRIPTION OF EMBODIMENTS

The present invention is described below.

(A) Zinc Oxide and/or Titanium Dioxide Hydrophobized with Octyltriethoxysilane and/or Dimethylpolysiloxane In the present invention, the hydrophobizing agents of zinc oxide and/or titanium dioxide are limited to octyltriethoxysilane and/or dimethylpolysiloxane. Using other hydrophobizing agents is detrimental to the dispersibility of the zinc oxide and/or titanium dioxide. The dimethylpolysiloxane has a degree of polymerization of preferably 100 to 1000.

The method used to hydrophobize zinc oxide and/or titanium dioxide is not particularly limited, and a surface treatment is performed according to an ordinary method. For example, zinc oxide and/or titanium dioxide may be mixed and stirred in octyltriethoxysilane and/or dimethylpolysiloxane for a certain time period, and filtered to produce zinc oxide and/or titanium dioxide hydrophobized with octyltriethoxysilane and/or dimethylpolysiloxane. Note that dimethylpolysiloxane is used in a liquid form that allows for hydrophobization.

The zinc oxide and/or titanium dioxide used in the present invention are fine powders, preferably fine powders having an average particle diameter of 10 to 80 nm.

The total content of the zinc oxide and/or titanium dioxide hydrophobized with octyltriethoxysilane and/or dimethylpolysiloxane is preferably 3 to 35 mass %, further preferably 5 to 30 mass %, most preferably 12 to 25 mass % with respect to the total amount of the oil-in-water emulsion sunscreen cosmetic.

The dispersibility of the zinc oxide and/or titanium dioxide may be adversely affected when the content of the zinc oxide and/or titanium dioxide hydrophobized with octyltriethoxysilane and/or dimethylpolysiloxane falls outside of these ranges.

(B) Liquid Higher Fatty Acid

The liquid higher fatty acid used in the present invention may be, for example, isostearic acid, oleic acid, linoleic acid, or linolenic acid. Particularly preferred is isostearic acid.

The liquid higher fatty acid as the oil component of the present invention is a component that, together with the dispersant component (C), forms an internal oil phase in the oil-in-water emulsion sunscreen cosmetic.

In the present invention, the hydrophobized zinc oxide or titanium dioxide (component (A)) is homogeneously dispersed in an oil phase formed by the oil component. The dispersibility of the zinc oxide or titanium dioxide lowers without the liquid higher fatty acid.

In the present invention, the hydrophobized zinc oxide or hydrophobized titanium dioxide (component (A)) is fully dispersed in the oil phase component to form an oil phase.

The oil component forming an oil phase may contain other oil components such as hydrocarbon oil (e.g., vaseline, and squalane), provided that such addition is not detrimental to the advantageous effects of the present invention. It is also preferable to contain a volatile oil component. Examples of a volatile oil component include a hydrocarbon oil of a relatively low molecular weight, a linear silicone of a relatively low molecular weight, and a cyclic silicone of a relatively low molecular weight. Particularly preferred are light liquid isoparaffin, isododecane, isohexadecane, and volatile dimethylpolysiloxane, or cyclic polysiloxane (for example, octamethylcyclotetrasiloxane, decamethylcyclopentasiloxane, dodecamethylcyclohexasiloxane, and hexadecamethylcycloheptasiloxane).

The content of the liquid higher fatty acid is preferably 0.1 to 2 mass %, further preferably 0.3 to 1.8 mass %, most preferably 0.5 to 1.5 mass % with respect to the total amount of the oil-in-water emulsion sunscreen cosmetic.

The dispersibility of the zinc oxide and/or titanium dioxide may be adversely affected when the liquid higher fatty acid content falls outside of these ranges.

(C) Silicone of Structure Containing Carboxyl Group or Sugar Ester (Dispersant)

The silicone of a structure containing a carboxyl group used in the present invention may be, for example, carboxydecyl trisiloxane, or alkylacrylate copolymer methylpolysiloxane ester. Particularly preferred is carboxydecyl trisiloxane.

The sugar ester used in the present invention may be, for example, sorbitan sesquiisostearate, dipentaerythritol fatty acid ester, polyoxyethylene sorbitan monooleate, or polyoxyethylene sorbitan monostearate. Particularly preferred is sorbitan sesquiisostearate.

In the present invention, the component (C) serves as a dispersant for homogeneously and stably dispersing the hydrophobized zinc oxide and/or hydrophobized titanium dioxide in the oil phase.

The content of the silicone of a structure containing a carboxyl group or the sugar ester is preferably 0.1 to 1.5 mass %, further preferably 0.2 to 1.2 mass %, most preferably 0.3 to 1.0 mass % with respect to the total amount of the oil-in-water emulsion sunscreen cosmetic.

The dispersibility of the zinc oxide and/or titanium dioxide may be adversely affected when the content of the silicone of a structure containing a carboxyl group or the sugar ester falls outside of these ranges.

(D) Non-Ionic Surfactant

The non-ionic surfactant used in the present invention is a component contained as an emulsifier for production of a stable oil-in-water emulsion composition. Preferably, a hydrophilic non-ionic surfactant is used in the present invention.

Specific examples of hydrophilic non-ionic surfactants include POE-sorbitan fatty acid esters (for example, POE-sorbitan monooleate, POE-sorbitan monostearate, POE-sorbitan tetraoleate); POE-sorbitol fatty acid esters (for example, POE-sorbitol monolaurate, POE-sorbitol monooleate, POE-sorbitol pentaoleate, POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, ethylene glycol distearate); POE-alkyl ethers (for example, POE-lauryl ether, POE-oleyl ether, POE-stearyl ether, POE-behenyl ether, POE-2-octyldodecyl ether, POE-cholestanol ether); Pluronic types (for example, Pluronic); POE.PPP-alkyl ethers (for example, POE.POP-cetyl ether, POE.POP-2-decyltetradecyl ether, POE.POP-monobutyl ether, POE.POP-hydrogenated lanolin, POE.POP-glycerin ether); tetra POE.tetra POP-ethylenediamine condensation products (for example, Tetronic); POE-castor oil-POE-hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, POE-hydrogenated castor oil maleic acid); POE-beeswax-lanolin derivatives (for example, POE-sorbitol beeswax); alkanolamides (for example, coconut oil fatty acid diethanolamide, lauric acid monoethanolamide, fatty acid isopropanolamide); POE-propylene glycol fatty acid esters; POEalkylamines; POE-fatty acid amides; sucrose fatty acid esters; alkylethoxydimethylamineoxide; and trioleyl phosphoric acid.

Examples of lipophilic non-ionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglyceryl sorbitan penta-2-ethylhexanoate, diglyceryl sorbitan tetra-2-ethylhexanoate); glycerin polyglycerin fatty acids (for example, cotton seed oil fatty acid monoglyceride, glyceryl monoerucate, glyceryl sesquioleate, glyceryl monostearate, α,α'-glyceryl oleate pyroglutamate, glyceryl monostearate malate); propylene glycol fatty acid esters (for example, propylene glycol monostearate); hydrogenated castor oil derivatives; and alkyl glyceryl ethers.

The content of the non-ionic surfactant is preferably 0.5 to 4.5 mass %, further preferably 1.0 to 4.0 mass % with respect to the total amount of the oil-in-water emulsion sunscreen cosmetic.

The stability of the oil-in-water emulsion cosmetic may lower when the non-ionic surfactant content falls outside of these ranges.

(E) Sodium Carboxymethyl Cellulose

The sodium carboxymethyl cellulose used in the present invention is an essential component for stably containing large amounts of the UV scattering agent (hydrophobized zinc oxide and/or hydrophobized titanium dioxide) in the internal phase of the oil-in-water emulsion composition of the present invention, and maintaining excellent emulsion stability. It has been extremely difficult with conventional techniques to stably contain large amounts of UV scattering agent (hydrophobized zinc oxide and/or hydrophobized titanium dioxide) in the internal phase of an oil-in-water emulsion composition.

With the combination of the essential components (A) to (E) of the present invention, the sodium carboxymethyl cellulose contained as component (E) allows large amounts of the UV scattering agent (hydrophobized zinc oxide and/or hydrophobized titanium dioxide) to be stably contained, and high levels of UV protection (high SPF) can be achieved while maintaining excellent emulsion stability, without containing an organic UV absorber. This is the key advantage of the present invention.

The content of the sodium carboxymethyl cellulose is preferably 0.1 to 1 mass %, further preferably 0.2 to 0.8 mass %, most preferably 0.3 to 0.6 mass % with respect to the total amount of the oil-in-water emulsion sunscreen cosmetic.

It may not be possible to stably contain large amounts of the UV scattering agent (hydrophobized zinc oxide and/or hydrophobized titanium dioxide) when the sodium carboxymethyl cellulose content falls outside of these ranges. In this case, the product may fail to provide high levels of UV protection, and may not be useful as a non-chemical sunscreen cosmetic.

(F) Water

The water used in the present invention is not particularly limited. Specific examples include purified water, and ion-exchange water.

Water is a component that, together with other aqueous components, forms an external aqueous phase in the oil-in-water emulsion cosmetic.

The water content is appropriately decided according to the content of the oil component forming the internal oil phase, and is preferably 20 to 55 mass %, further preferably 25 to 45 mass % with respect to the total amount of the oil-in-water emulsion sunscreen cosmetic.

The stability of the oil-in-water emulsion cosmetic may suffer, or a pleasant moisturizing feel may not be obtained, when the water content falls outside of the foregoing ranges.

Containing No Organic UV Absorber

The oil-in-water emulsion sunscreen cosmetic of the present invention is a non-chemical sunscreen cosmetic that does not contain any organic UV absorber. Despite that an organic UV absorber is not contained, the oil-in-water emulsion sunscreen cosmetic of the present invention can provide high levels of UV protection (high SPF) because of the large amounts of the UV scattering agent stably contained therein.

The following lists include examples of specific compounds typically contained as organic UV absorbers in common sunscreen cosmetics. However, none of these organic UV absorbers are contained in the present invention.

(1) Benzoic Acid UV Absorber

Examples include para-aminobenzoic acid (hereinafter, simply "PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester.

(2) Anthranilate UV Absorber

Examples include homomenthyl-N-acetylanthranilate.

(3) Salicylate UV Absorber

Examples include amyl salicylate, menthyl salicylate, homomenthyl salicylate, octyl salicylate, phenyl salicylate, benzyl salicylate, and p-isopropanol phenyl salicylate.

(4) Cinnamate UV Absorber

Examples include octyl cinnamate, ethyl-4-isopropyl cinnamate, methyl-2,5-diisopropyl cinnamate, ethyl-2,4-diisopropyl cinnamate, methyl-2,4-di isopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-di-p-methoxy cinnamate.

(5) Triazine UV Absorber

Examples include bis-resorcinyl triazine.

Further specific examples include bis{[4-(2-ethylhexyloxy)-2-hydroxy]phenyl}-6-(4-methoxyphenyl)-1,3,5-triazine, and 2,4,6-tris{4-(2-ethylhexyloxycarbonyl)anilino}-1,3,5-triazine.

(6) Other Organic UV Absorber

Examples include 3-(4'-methylbenzylidene)-d, 1-camphor, 3-benzylidene-d, 1-camphor, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dianisoylmethane, 4-methoxy-4'-t-butyldibenzoylmethane, 5-(3,3-dimethyl-2-norbornylidene)-3-pentan-2-one, and pyridazine derivatives such as dimorpholino pyridazinone.

Oil-in-Water Emulsion Cosmetic

In addition to the foregoing essential components, the oil-in-water emulsion sunscreen cosmetic of the present invention may appropriately contain components contained in common cosmetics, provided that it is not detrimental to the advantageous effects of the present invention. Examples of such additional components include moisturizers, thickeners, powders, alcohols, natural polymers, synthetic high polymers, sugars, antioxidants, buffers, various extracts, stabilizers, preservatives, dyes, and flavors.

In the oil-in-water emulsion sunscreen cosmetic producing process of the present invention, the zinc oxide and/or titanium dioxide hydrophobized with octyltriethoxysilane and/or dimethylpolysiloxane (component (A)) are dispersed to form an oil phase by being mixed and stirred in an oil component containing the highly dispersive liquid higher fatty acid (component (B)) and the dispersant (component (C)), using an HM mixer or the like. On the other hand, water (component (F)), the hydrophilic non-ionic surfactant (component (D)), the sodium carboxymethyl cellulose (component (E)), and aqueous components such as ethanol, a thickener, and a moisturizer are mixed to form an aqueous phase. The aqueous phase and the oil phase are then emulsified by using an ordinary method to provide the oil-in-water emulsion sunscreen cosmetic of the present invention.

The oil-in-water emulsion sunscreen cosmetic of the present invention is an emulsion composition with exceptional emulsion stability.

The non-chemical oil-in-water emulsion sunscreen cosmetic of the present invention uses zinc oxide and/or titanium dioxide powder as a UV scattering agent, and these are homogeneously dispersed in the oil phase. The non-chemical oil-in-water emulsion sunscreen cosmetic of the present invention thus does not give a powdery feel, but has a very pleasant moisturizing feel, making it preferable for use as, for example, a sunscreen emulsion, or a sunscreen cream.

Further, because the zinc oxide or titanium dioxide may be stably contained in large amounts, the non-chemical oil-in-water emulsion sunscreen cosmetic of the present invention does not give a powdery feel, and can provide high levels of UV protection even if a pleasant moisturizing feel is given priority. The non-chemical oil-in-water emulsion sunscreen cosmetic of the present invention can thus be expected to provide levels of UV protection comparable to or greater than that of an oil-in-water emulsion sunscreen cosmetic that does not prioritize a pleasant feel.

EXAMPLES

The present invention is described below in greater detail using Examples. It should be noted, however, that the present invention is not limited by the descriptions of the following Examples. In the following, contents are in mass % with respect to the total amount, unless otherwise stated.

Emulsions (oil-in-water emulsion sunscreen cosmetics) were produced with the formulations presented in Tables 1 and 2, using an ordinary method. These were evaluated in the manner described below.

Emulsion Stability: Dispersibility of Hydrophobized Zinc Oxide and/or Hydrophobized Titanium Dioxide The emulsions of Examples and Comparative Examples immediately after production were each charged into a cylindrical container in about half the volume of the container, and rotated at 45 rpm for 2 hours at room temperature (25 to 30° C.). The dispersed state of the hydrophobized zinc oxide and/or hydrophobized titanium dioxide was then visually observed with a light microscope (400 times magnification), and examined according to the following evaluation criteria.

Evaluation Criteria

Good: There was no state change after the test, and the emulsion state was stable. Specifically, the fine particles of hydrophobized zinc oxide or titanium dioxide were homogeneously dispersed in the oil phase.

Acceptable: The fine particles of hydrophobized zinc oxide or titanium dioxide were not homogeneously dispersed in the oil phase, and were unevenly distributed.

Poor: The hydrophobized zinc oxide and/or hydrophobized titanium dioxide escaped from the dispersed oil phase to the aqueous phase.

Powdery Feel

A demonstration test was conducted by applying the emulsions to the arm of 10 trained panelists. The results were evaluated according to the following criteria.

Evaluation Criteria

Good: At least 8 out of the 10 testers felt no powdery feel.
Acceptable: 5 to 7 out of the 10 testers felt no powdery feel.
Poor: Less than 5 out of the 10 testers felt no powdery feel.

Moisturizing Feel

A demonstration test was conducted by applying the emulsions to the arm of 10 trained panelists. The results were evaluated according to the following criteria.

Evaluation Criteria

Good: At least 8 out of the 10 testers felt a moisturizing feel.
Acceptable: 5 to 7 out of the 10 testers felt a moisturizing feel.
Poor: Less than 5 out of the 10 testers felt a moisturizing feel.

TABLE 1

| | | | Com. Ex. 1 | Com. Ex. 2 | Ex. 1 | Ex. 2 | Ex. 3 | Ex. 4 |
|---|---|---|---|---|---|---|---|---|
| Water | F | (1) Water | Remainder | Remainder | Remainder | Remainder | Remainder | Remainder |
| Alcohol | | (2) Ethanol | 5 | 5 | 5 | 5 | 5 | 5 |
| Moisturizer | | (3) Glycerin | 3 | 3 | 3 | 3 | 3 | 3 |
| Thickener | | (4) Succinoglycan | 0.3 | 0.3 | 0.3 | 0.3 | 0.3 | 0.3 |
| | | (5) (Dimethylacrylamide/sodium acryloyl dimethyl taurate)crosspolymer | 0.3 | 0.3 | 0.3 | 0.3 | 0.3 | 0.3 |
| Stabilizer | E | (6) Sodium carboxymethyl cellulose | 0 | 0.1 | 0.2 | 0.3 | 0.5 | 0.3 |
| Surfactant | D | (7) Polyoxyethylene hydrogenated castor oil | 3 | 3 | 3 | 3 | 3 | 3 |
| Oil component | | (8) Squalane | 10 | 10 | 10 | 10 | 10 | 10 |
| | | (9) Glyceryl tri(caprylate/caprate) | 10 | 10 | 10 | 10 | 10 | 10 |
| | | (10) Dimethylpolysiloxane (6 cs) | 5 | 5 | 5 | 5 | 5 | 5 |
| Dispersant | C | (11) Sorbitan sesquiisostearate | 0.5 | 0.5 | 0.5 | 0.5 | 0.5 | |
| | C | (12) Carboxydecyl trisiloxane | | | | | | 0.5 |
| Liquid higher fatty acid | B | (13) Isostearic acid | 1 | 1 | 1 | 1 | 1 | 1 |

TABLE 1-continued

| | | | Com. Ex. 1 | Com. Ex. 2 | Ex. 1 | Ex. 2 | Ex. 3 | Ex. 4 |
|---|---|---|---|---|---|---|---|---|
| Hydrophobized zinc oxide | A | (14) Octyltriethoxysilane-treated zinc oxide | 16 | 16 | 16 | 16 | 16 | 16 |
| Hydrophobized titanium dioxide | A | (15) Octyltriethoxysilane-treated titanium dioxide | 4 | 4 | 4 | 4 | 4 | 4 |
| Powder | | (16) Silica | 1 | 1 | 1 | 1 | 1 | 1 |
| Buffer | | (17) Sodium citrate | Appropriate amount | Appropriate amount | Appropriate amount | Appropriate amount | Appropriate amount | Appropriate amount |
| | | (18) Citric acid | Appropriate amount | Appropriate amount | Appropriate amount | Appropriate amount | Appropriate amount | Appropriate amount |
| Chelating agent | | (19) Chelating agent | Appropriate amount | Appropriate amount | Appropriate amount | Appropriate amount | Appropriate amount | Appropriate amount |
| Preservative | | (20) Phenoxy ethanol | 0.5 | 0.5 | 0.5 | 0.5 | 0.5 | 0.5 |
| | | Emulsion stability | Poor | Acceptable | Good | Good | Good | Good |

Method of Production

Preparation of Aqueous Phase

Components (17), (18), (19), and (20) were added and dissolved in component (1). Components (4), (5), and (6) were wetted with component (3), and the resultant was mixed with component (1).

Preparation of Oil Phase

Components (8), (9), (10), (11), (12), and (13) were homogeneously mixed, components (14) and (15) were added to the mixture, and the resultant was dispersed with an HM mixer.

Preparation of Oil-in-Water Emulsion Composition

Component (7) was mixed with the aqueous phase (70° C.), and the oil phase was emulsified. After adding the parts of components (2) and (16) as a mixture, the whole was cooled to obtain an emulsion.

TABLE 2

| | | | Com. Ex. 3 Water-in-oil emulsion | Ex. 3 Oil-in-water emulsion |
|---|---|---|---|---|
| Water | F | (1) Water | Remainder | Remainder |
| Alcohol | | (2) Ethanol | 5 | 5 |
| Moisturizer | | (3) Glycerin | 3 | 3 |
| Thickener | | (4) Succinoglycan | 0 | 0.3 |
| | | (5) (Dimethylacrylamide/sodium acryloyl dimethyl taurate) crosspolymer | 0 | 0.3 |
| | | (6) Dimethyl distearyl ammonium hectorite | 2 | 0 |
| Stabilizer | E | (7) Sodium carboxymethyl cellulose | 0 | 0.3 |
| Surfactant | D | (8) Polyoxyethylene hydrogenated castor oil | 0 | 3 |
| | | (9) Lauryl PEG-9 polydimethylsiloxy ethyldimethicone | 3 | 0 |
| Oil component | | (10) Squalane | 2 | 10 |
| | | (11) Glyceryl tri(caprylate/caprate) | 2 | 10 |
| | | (12) Decamethylcyclopentasiloxane | 10 | 0 |
| | | (13) Dimethylpolysiloxane (6 cs) | 5 | 5 |
| Dispersant | C | (14) Sorbitan sesquiisostearate | 0.5 | 0.5 |
| Liquid higher fatty acid | B | (15) Isostearic acid | 1 | 1 |
| Hydrophobized zinc oxide | A | (16) Octyltriethoxysilane-treated zinc oxide | 16 | 16 |
| Hydrophobized titanium dioxide | A | (17) Octyltriethoxysilane-treated titanium dioxide | 4 | 4 |
| Powder | | (18) Silica | 1 | 1 |
| Buffer | | (19) Sodium citrate | Appropriate amount | Appropriate amount |
| | | (20) Citric acid | Appropriate amount | Appropriate amount |
| Chelating agent | | (21) Chelating agent | Appropriate amount | Appropriate amount |
| Preservative | | (22) Phenoxy ethanol | 0.5 | 0.5 |
| Feeling (n = 10) | | Powdery feel | Poor | Good |
| | | Moisturizing feel | Poor | Good |
| UV spectrum | | The levels of UV protection were essentially the same, as shown in the UV spectra of FIG. 1. | Solid circle | Solid diamond |

Method of Production

Emulsions (oil-in-water emulsion sunscreen cosmetics) of Example 3 and Comparative Example 3 were produced according to the producing method of Examples presented in Table 1.

It can be seen from Tables 1 and 2 that the oil-in-water emulsion sunscreen cosmetics of Examples 1 to 4 containing all of the essential components of the present invention excelled in both hydrophobic emulsion stability and pleasant feel.

The oil-in-water emulsion sunscreen cosmetics of Example 3 and Comparative Example 3 that contained the same amounts of the hydrophobized zinc oxide and hydrophobized titanium dioxide as a UV scattering agent had essentially the same levels of organic UV absorber protection as observed in the UV spectra. As demonstrated above, the levels of UV protection remain the same, and do not drop even when a pleasant feel is given priority as in Example 3.

The configuration of the present invention allows large amounts of hydrophobized zinc oxide and hydrophobized titanium dioxide to be stably contained as a UV scattering agent in the oil-in-water emulsion composition, and provides a pleasant feel. High levels of UV protection can thus be obtained as desired by increasing the UV scattering agent content.

The emulsions of Examples 1 to 4 of the present invention represent oil-in-water emulsion sunscreen cosmetics that do not give a powdery feel, but provide a pleasant moisturizing feel. These oil-in-water emulsion sunscreen cosmetics were also able to suppress the attribute that the whiteness of the UV scattering agent becomes noticeable upon application.

INDUSTRIAL APPLICABILITY

The present invention can provide an organic UV absorber-free, non-chemical sunscreen cosmetic that contains hydrophobized zinc oxide and/or hydrophobized titanium dioxide as a UV scattering agent, specifically an oil-in-water emulsion sunscreen cosmetic that provides excellent emulsion stability and an excellent pleasant feel with the hydrophobized zinc oxide and/or hydrophobized titanium dioxide homogeneously and stably dispersed as a UV scattering agent in the oil phase.

According to the present invention, a non-chemical sunscreen cosmetic that provides high levels of UV protection can be designed without containing an organic UV absorber, because the cosmetic can stably contain large amounts of hydrophobized zinc oxide and/or hydrophobized titanium dioxide as a UV scattering agent. Further, because the cosmetic does not give a powdery feel, but provides a pleasant moisturizing feel, the present invention is very useful as an oil-in-water emulsion sunscreen cosmetic.

The invention claimed is:

1. An organic UV absorber-free, oil-in-water emulsion sunscreen cosmetic that comprises:
   (A) zinc oxide and/or titanium dioxide;
   (B) isostearic acid;
   (C) a silicone containing a carboxyl group;
   (D) a non-ionic surfactant;
   (E) sodium carboxymethyl cellulose; and
   (F) water;
   wherein said (A) zinc oxide and/or titanium dioxide is:
   hydrophobized with octyltriethoxysilane and/or dimethylpolysiloxane; and
   homogeneously dispersed in an oil phase with said (C) silicone containing a carboxyl group acting as a dispersant; and
   wherein the dispersibility of the zinc oxide or the titanium dioxide lowers without said (B) isostearic acid wherein (C) the silicone containing a carboxyl group is carboxydecyl trisiloxane.

2. The oil-in-water emulsion sunscreen cosmetic according to claim 1, wherein the contents of the components (A) to (E) with respect to the total amount of the oil-in-water emulsion sunscreen cosmetic are:
   3 to 35 mass % for (A) the zinc oxide and/or the titanium dioxide hydrophobized with octyltriethoxysilane and/or dimethylpolysiloxane;
   0.1 to 2 mass % for (B) the isostearic acid;
   0.1 to 1.5 mass % for (C) the silicone containing a carboxyl group;
   0.5 to 4.5 mass % for (D) the non-ionic surfactant; and
   0.1 to 1 mass % for (E) the sodium carboxymethyl cellulose.

3. The oil-in-water emulsion sunscreen cosmetic according to claim 1, further comprising:
   (G) a natural polymer or a synthetic high polymer.

4. The oil-in-water emulsion sunscreen cosmetic according to claim 2, further comprising:
   (G) a natural polymer or a synthetic high polymer.

5. A method for making the organic UV absorber-free, oil-in-water emulsion sunscreen cosmetic of claim 1, the method comprising the steps of:
   hydrophobizing (A) the zinc oxide and/or titanium dioxide with octyltriethoxysilane and/or dimethylpolysiloxane; and
   dispersing the hydrophobized zinc oxide and/or titanium dioxide homogeneously in an oil phase with (C) carboxydecyl trisiloxane acting as a dispersant;
   wherein the dispersibility of the zinc oxide or the titanium dioxide lowers without (B) the isostearic acid.

* * * * *